United States Patent [19]

Zuber et al.

[11] 4,196,635
[45] Apr. 8, 1980

[54] TEST APPARATUS FOR THE SIMULTANEOUS LOADING OF A TEST SAMPLE WITH LONGITUDINAL FORCES AND WITH TORQUE

[75] Inventors: Günter Zuber; Karlheinz Storck, both of Darmstadt, Fed. Rep. of Germany

[73] Assignee: Carl Schenck AG, Darmstadt, Fed. Rep. of Germany

[21] Appl. No.: 960,912

[22] Filed: Nov. 15, 1978

[30] Foreign Application Priority Data

Dec. 23, 1977 [DE] Fed. Rep. of Germany ....... 2757541

[51] Int. Cl.² .......................... G01N 3/10; G01N 3/22
[52] U.S. Cl. .................................................... 73/794
[58] Field of Search ................... 73/9, 794, 795, 814, 73/837, 847, 848

[56] References Cited

U.S. PATENT DOCUMENTS 3,338,092   8/1967   Lindholm et al. ...................... 73/794

FOREIGN PATENT DOCUMENTS 1024245   3/1966   United Kingdom ...................... 73/795

*Primary Examiner*—Charles A. Ruehl
*Attorney, Agent, or Firm*—W. G. Fasse; D. F. Gould

[57] ABSTRACT

The present test apparatus provides for the simultaneous loading of a test sample with longitudinal forces and with torque. For this purpose a piston rod of a longitudinal loading cylinder and a piston of a torque cylinder are coupled for relative axial movement by a fork connected to the piston rod of the longitudinal loading cylinder and guided in a torque transmitting member connected to the piston of the torque cylinder. Frictional forces and play are minimized by providing the fork ends with bearing surfaces and providing the torque transmitting member with both stationary and tiltable bearings which may be adjustable. Another embodiment provides that the bearings of the torque transmitting member are hydrostatic bearings to further reduce friction.

12 Claims, 5 Drawing Figures

TEST APPARATUS FOR THE SIMULTANEOUS LOADING OF A TEST SAMPLE WITH LONGITUDINAL FORCES AND WITH TORQUE

BACKGROUND OF THE INVENTION

The invention relates to a test apparatus for the simultaneous loading of a test sample with longitudinal forces and with torque moments. The test apparatus comprises a machine frame, e.g., a two post machine frame, a hydraulic loading cylinder attached to the machine frame for producing the longitudinal forces and a hydraulic rotating piston cylinder arrangement for producing the torque or torque moment.

Testing devices for the simultaneous loading of a test sample with longitudinal forces and torque moments are known which have so-called "rotating cylinders" attached to the piston rod of said hydraulic loading cylinder. So-called "rotating cylinders" operate in accordance with the vane or wing principle. A rotary piston is rotatably mounted in a sealed manner within a casing and is provided with one or two inwardly directed wings or lands. When a pressure medium is fed into the chambers formed by the housing and the rotary piston, the rotary piston may be rotated approximately ±150° or ±60° from its central position relative to the casing. When the casing is immovably secured, torque may thus be produced by the rotary piston. Such torque may, for example, be transmitted to a test sample. The combination of a longitudinal loading cylinder with a rotating piston cylinder device thus permits the simultaneous production of longitudinal forces and torque moments and a corresponding loading of the test samples.

The rotating cylinder of a known arrangement is attached to the piston rod of the longitudinal loading cylinder and is moved along with the longitudinal movements of the longitudinal loading piston cylinder. The piston rods of the longitudinal loading cylinder and of the rotating piston cylinder are securely fastened to each other. The piston rods and the pistons perform the longitudinal and rotary movement together. The housing of the rotating piston cylinder is guided longitudinally and is supported in the direction of rotation on the stationary portion of the testing apparatus so that the torque may be transmitted to the test sample which is connected to the rotary piston. The longitudinal force is transmitted to the test sample through the rotary piston.

The rotating cylinder with its supply lines for the pressure medium is subjected to heavy loading during larger longitudinal movements and at higher test frequencies. In addition, undesired inertial forces and considerable frictional force occur in the longitudinal guide means required for the rotating cylinder. Another disadvantage is seen in that circumferential play may be eliminated only with difficulty. The loading of the test sample and the test results respectively may be influenced by these factors.

OBJECTS OF THE INVENTION

In view of the above it is the aim of the invention to achieve the following objects singly or in combination:

to construct a testing apparatus which avoids the disadvantages of the prior art when simultaneously loading a test sample with longitudinal forces and torque;

to provide such an apparatus wherein a cylinder with a rotating piston may be rigidly installed in a fixed position thus eliminating excessive loads to the cylinder and the supply lines;

to provide such an apparatus which eliminates the influence of the mass of the rotating cylinder on the loading of the test sample or the measurement thereof by transmitting torque moments without or substantially without play;

to provide a testing apparatus wherein the frictional forces during longitudinal movement are minimized;

to provide a testing apparatus which may transmit torque and rotary movement without play; and to provide such an apparatus wherein the above objects are achieved by using simple structural means.

SUMMARY OF THE INVENTION

According to the invention, the present testing apparatus comprises a machine frame wherein a rotating piston cylinder arrangement is rigidly mounted on that side of the longitudinal loading piston cylinder which is opposite to the side to which the test sample is connected. The axis of rotation of the rotating piston cylinder extends in alignment with the axis of the longitudinal loading piston cylinder. A fork shaped component or fork is connected to the free end of the piston rod of the longitudinal loading piston cylinder between the latter and the rotating piston cylinder. The fork ends of the fork shaped component are longitudinally movable but not rotatable relative to a torque transmitting member connected to the piston rod of the rotating piston cylinder. Thus, the fork rotates with the torque transmitting member.

One preferred embodiment of the invention is seen in that the housing of the longitudinal loading piston cylinder is connected to the housing of the rotating piston cylinder by means of a secondary frame member, into which one piston rod end of the longitudinal loading piston and the piston rod of the rotating piston cylinder extend in a rotatable manner. By rigidly mounting the rotary piston cylinder excessive loads on the latter and its connecting lines are avoided. Similarly, the load on the test sample and the measured results are not adversely affected by the mass of the rotating cylinder. The guiding of the fork may be accomplished by relatively simple means substantially free of friction and play.

A further embodiment of the invention which substantially avoids frictional forces during longitudinal movement is seen in that each fork end has bearing surfaces on both sides and two roller bearings are arranged on each side of the torque transmitting member for longitudinally guiding the fork ends and for transmitting torque. The bearing surfaces of the fork ends are guided between the roller bearings.

BRIEF FIGURE DESCRIPTION

In order that the invention may be clearly understood, it will now be described by way of example, with reference to the accompanying drawings, wherein.

DETAILED DESCRIPTION OF PREFERRED EXAMPLE EMBODIMENTS

Figure 1:
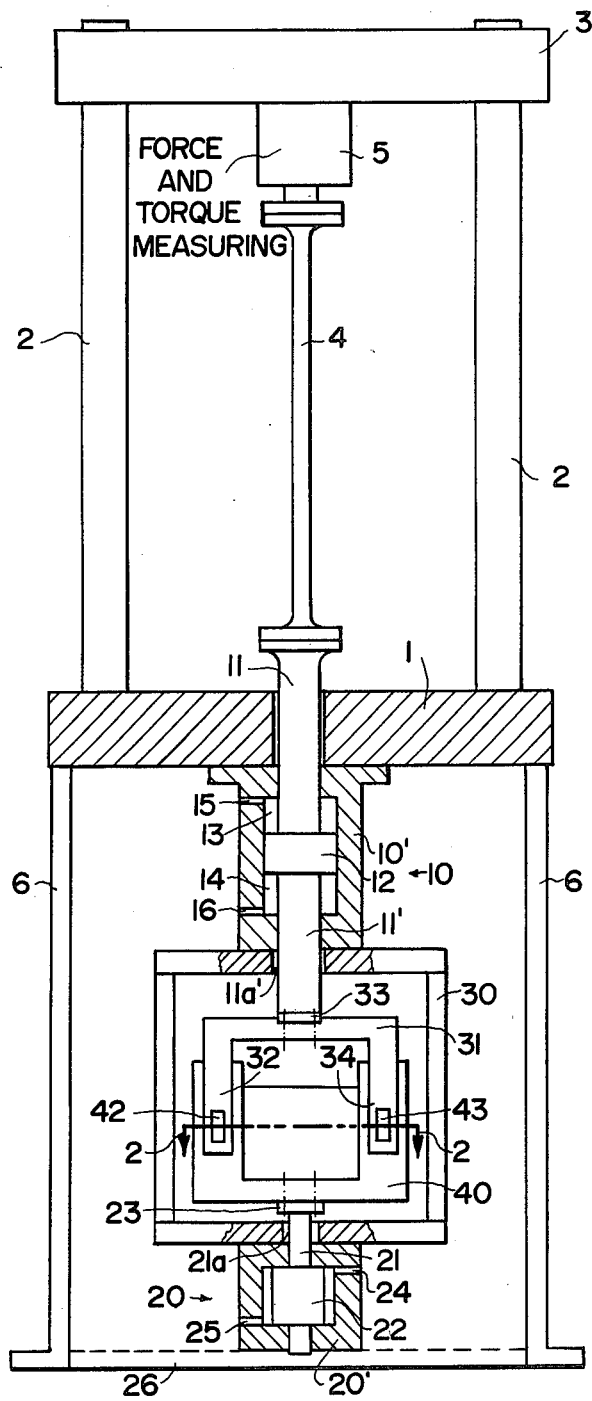
FIG. 1 is substantially an elevational front view of the present testing apparatus and partially in section.

FIG. 1 shows a main machine frame with a base plate 1, posts 2 and a crown or cross beam 3. The machine frame may be of any desired type well known in the construction of testing machines, e.g., a two or four post frame may be used. At test sample 4 is mounted between the base plate 1 and the crown 3 and may, for example, be connected to the crown 3 through a device 5 for measuring force and torque.

A longitudinal loading piston cylinder 10 is mounted beneath the base plate 1. The piston rod 11 of the longitudinal loading piston cylinder 10 extends through an opening in the base plate 1 and is connected to the test sample 4. Forces (pressure, tension, and alternating loads) may be applied to the test sample 4 by a piston 12 in the longitudinal loading piston cylinder and the piston rod 11 by the feeding of a pressure medium into the cylinder chambers 13, 14 through the connections 15, 16 in a known manner. It is known, how to provide the pressure medium and how to control such testing apparatus.

A secondary frame component 30 is connected to the longitudinal loading piston cylinder and firmly connects the longitudinal loading cylinder 10 to a rotating piston cylinder 20. The longitudinal loading piston cylinder 10 and the rotating piston cylinder 20 are arranged coaxially. The piston rod end 11' of the longitudinal loading cylinder 10 and the piston rod 21 of a rotary piston 22 extend through holes 11a' and 21a respectively and into the secondary frame component 30. The secondary frame component 30 is built as torsionally rigid as possible since it must take up and transmit the torque which occurs between the casing 20' of the rotating piston cylinder 20 and the casing 10' of the longitudinal loading cylinder 10.

Figure 2:
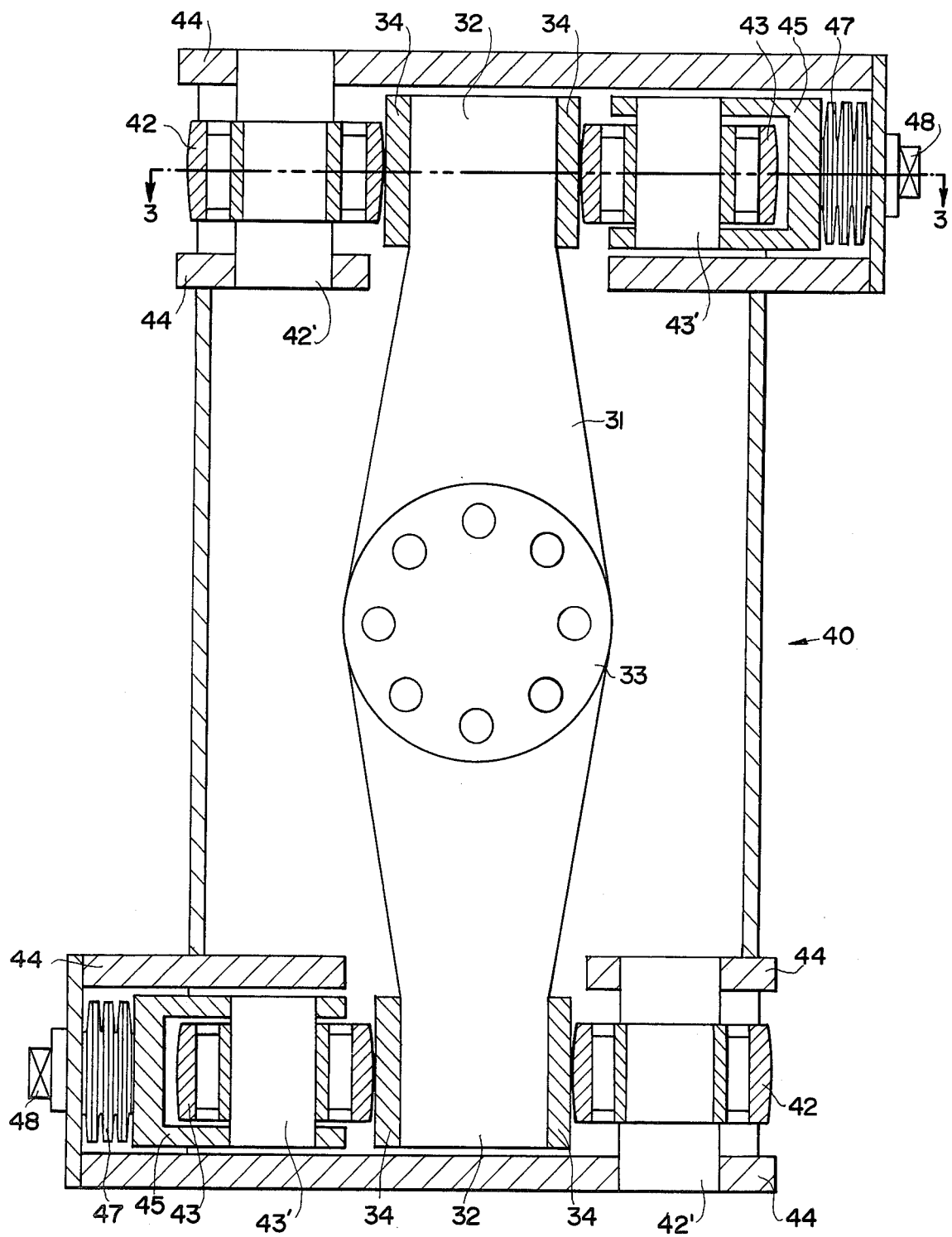
FIG. 2 shows on an enlarged scale a sectional view along section line 2—2 in FIG. 1 of the clutch connection rotated by 90° with a top plan view of a fork member superimposed on the section and with the fork member in its working position.

A fork member 31 is arranged on the piston rod end 11' of the longitudinal loading piston cylinder 10 and, for example, it is firmly connected to the piston rod 11' by means of a flange fitting 33 shown in FIG. 2. The piston rod 21 of the rotating piston cylinder 22 has a flange connector 23 which is firmly secured to a torque transmitting member 40. The torque transmitting member 40 serves to guide the fork ends 32 of the fork member 31.

The rotating piston cylinder 20 or rather the rotary piston 22 may be loaded by means of a pressure medium through the connections 24, 25, whereby torque or rotary movement, for example, up to about ±60° may be produced through the piston rod 21 or through the connecting flange 23 of the rotary piston 22. The torque or rotary movement will be transmitted by the torque transmitting member 40 and the fork ends 32 of the fork member 31 to the piston rod 11', 11 whereby the latter applies the torque to the test sample 4.

Longitudinal forces or longitudinal movement respectively as well as torque or rotary movement respectively may be transmitted to the test sample 4 by the simultaneous actuation of the piston 12 in the longitudinal loading piston cylinder 10 and the rotary piston 22 in the rotating piston cylinder 20. During longitudinal movement, the fork member 31 slides in the guideway of the torque transmitting member 40 with both fork ends 32. The piston rods 11, 11' and the piston 12 in the longitudinal loading piston cylinder 10 are also twisted during rotary movement of the rotary piston 22.

Figure 3:
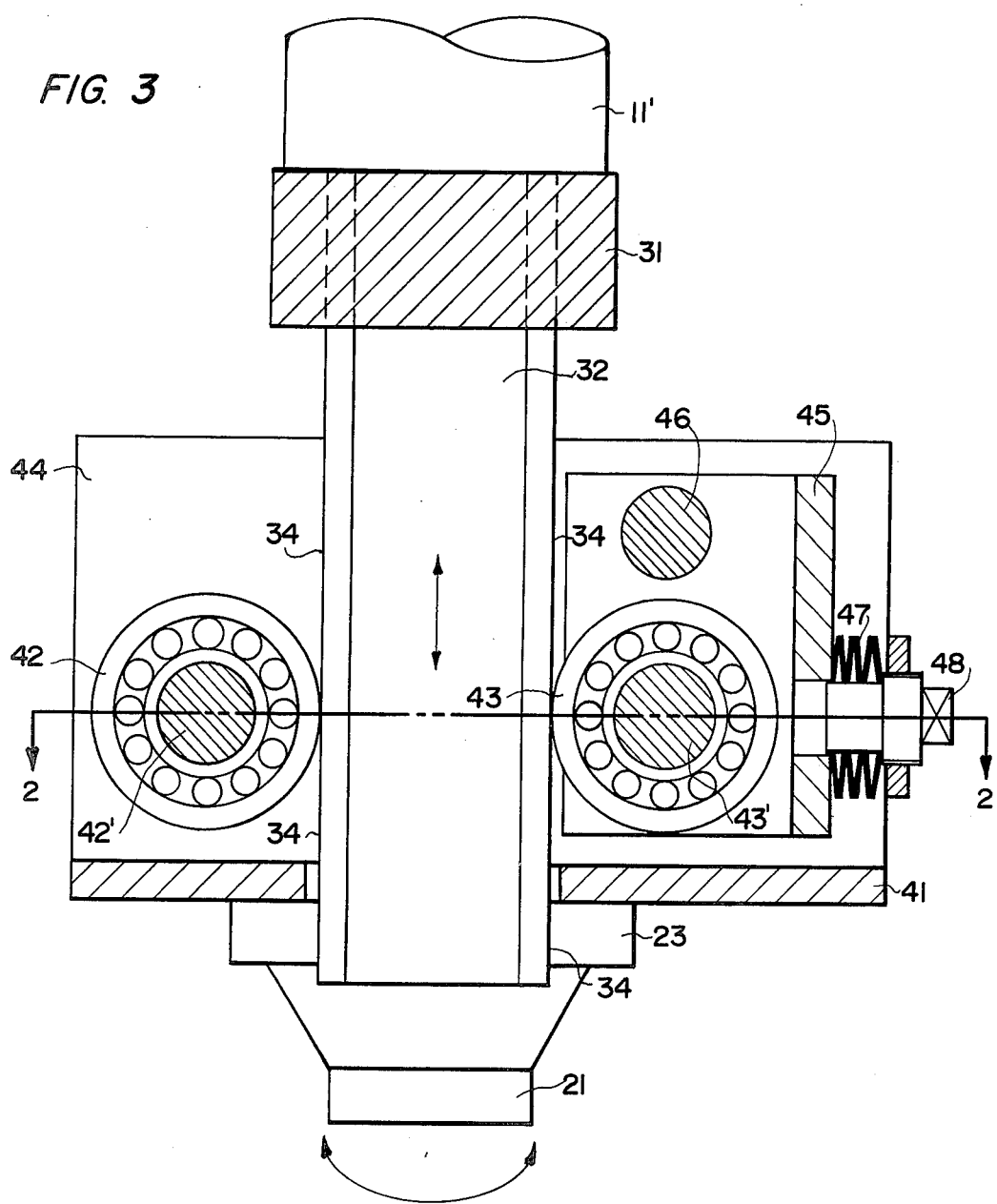
FIG. 3 is a partially sectional view along section line 3—3 in FIG. 2 showing a torque transmitting fork member with roller bearings.

FIGS. 2 and 3 further describe the details of the coupling connection between the longitudinal piston cylinder 10 and the torque producing cylinder 20. As stated above, the fork member 31 is connected to the facing end of the piston rod 11' by means of a flange fitting 33. The connection between the piston rod 11' and the fork member 31 may also be provided by any other suitable connecting means. The fork ends 32 have smooth bearing surfaces on both sides and these bearing surfaces extend in parallel to one another. The fork member may, for example, be constructed by welding.

The torque transmitting member 40 is connected by means of its base plate 41 through the connecting flange 23 to the piston rod 21 or to the rotary piston 22 of the torque producing cylinder 20 whereby the member 40 follows the rotary movement of the rotary piston 22. Two shafts 42' of the roller bearings 42 with the respective rollers are rigidly arranged in arms 44 of the torque transmitting member 40. Two additional roller bearings 43 are mounted on shafts 43' so that they are tiltable toward the respective bearing surface. For this tilting purpose housings 45 are arranged between the arms 44. The housings 45 hold the bearings 43 with the respective shafts 43'. The housings are tiltable about axles 46 extending in parallel to the roller shafts.

The tiltable roller bearings 43 are biased against the respective fork ends 32 by means of adjustable springs such as Belleville springs 47, whereby the housings 45 and thus the rollers of the bearings 43 may be pressed against the bearing surfaces 34 of said fork ends 32. The spring bias is preferably adjustable by well known means such as a nut 48. The fork ends or bearing surfaces thus bear against the fixed roller bearings 42. By selecting the bias tension of the springs 47 the contact between the fork ends 32 and the roller bearings 42, 43 may be maintained free of play for the torques to be transferred. Production inaccuracies may be compensated due to the arrangement of the adjustable rollers 43 diagonally opposite each other as best seen in FIG. 2. In addition, it is possible to uniformly adjust the rollers by the nuts 48.

Figure 4:
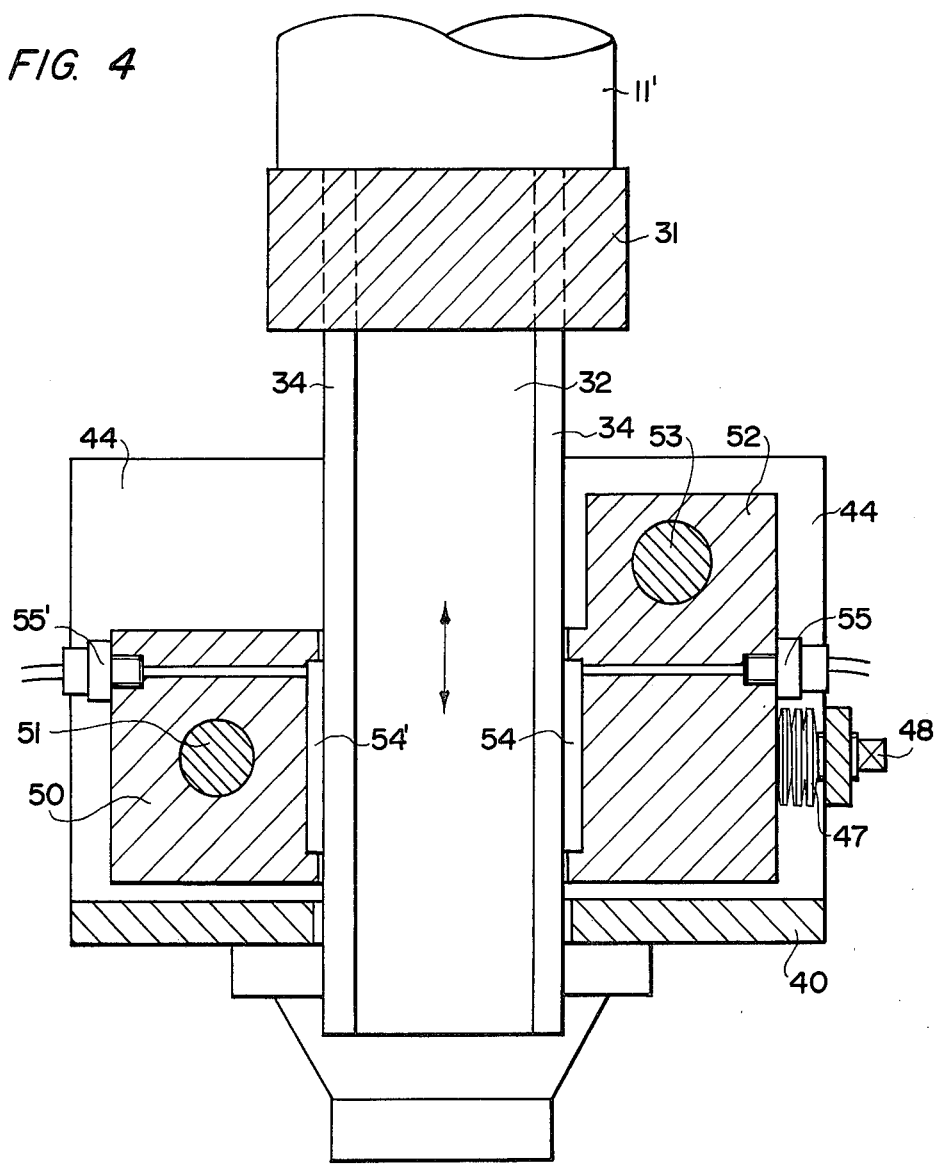
FIG. 4 is a partially sectional view of another embodiment of a torque transmitting member substantially along section line 3—3 in FIG. 2, however, with the roller bearings replaced by hydrostatic bearings.

FIG. 4 shows another advantageous embodiment of the invention wherein the torque transmitting member 40 comprises hydrostatic bearings for guiding the fork ends 32 and wherein said hydrostatic bearings are adjustable by means of said springs 47 and nuts 48. This arrangement results in particularly small frictional forces during the transmittal of torque moments or during longitudinal movements of the piston rod 11' of the longitudinal loading piston cylinder 10, since only fluid friction occurs in the guideways. Simultaneously a substantially play free coupling is accomplished between the longitudinal piston cylinder 10 and the torque producing cylinder 20. The corresponding fork ends of FIG. 4 wherein only one fork end is shown as in FIG. 3 are supported hydrostatically. The fork member 31 which is secured to the piston rod 11' of the longitudinal piston cylinder 10, the fork ends 32 of the fork member 31, and the torque transmitting member 40 correspond essentially to the arrangement shown in FIGS. 2 and 3. In place of the roller bearings, however, hydrostatic bearings are provided in FIG. 4 for guiding and supporting the fork ends 32.

The bearing structure of FIG. 4 comprises a bearing member 50 which is tiltably arranged on an axis 51 between the arms 44 of the torque transmitting member 40. The tiltable arrangement is provided so that the bearing member may adapt itself to any elastic distortions of the fork ends. A further bearing member 52 is located on the opposite side and is also tiltable about an axis 53 extending in parallel to the axis 51 between the arms 44. The bearing members have bearing pockets 54, 54' which are supplied with a pressure medium through the supply lines 55, 55'. Thus, a pressure medium film is formed in a known manner in the bearing gap between the bearing members 50, 52 and the bearing surfaces or guiding surfaces 34 of the fork ends 32. Such film results in a particularly low friction when the fork 31 moves longitudinally relative to the torque member 40 as shown by the double arrow in FIG. 4. The leakage oil escaping out of the bearing gaps between the bearings and the bearing surfaces may be collected and drained by appropriate means not shown since such means are known.

The bearing or guiding surfaces 34 of the fork ends 32 and the corresponding opposing surfaces of the bearing members 50, 52 may be flat as shown in FIGS. 2 and 3 or they may be cylindrical. In such an embodiment the fork ends may also have a round cross-section.

As stated, the bearing members 50, 52 are arranged for tilting on axes 41, 53, hence these bearing members may adjust themselves to any elastic deforming of the fork ends 32. In this way the guiding action of the bearings is improved. In addition, the bearing member 52, similar to the roller 43 of the housing 45 of FIGS. 2 and 3, is pressed against the fork end by the Belleville spring 47 by means of the adjusting nut 48. The adjustability of the bearing members 50, 52 may also be assured by other means, for example, by suitable guide means or adjustable bearings. Other embodiments of hydrostatic bearings may be provided instead of the one shown.

Figure 5:
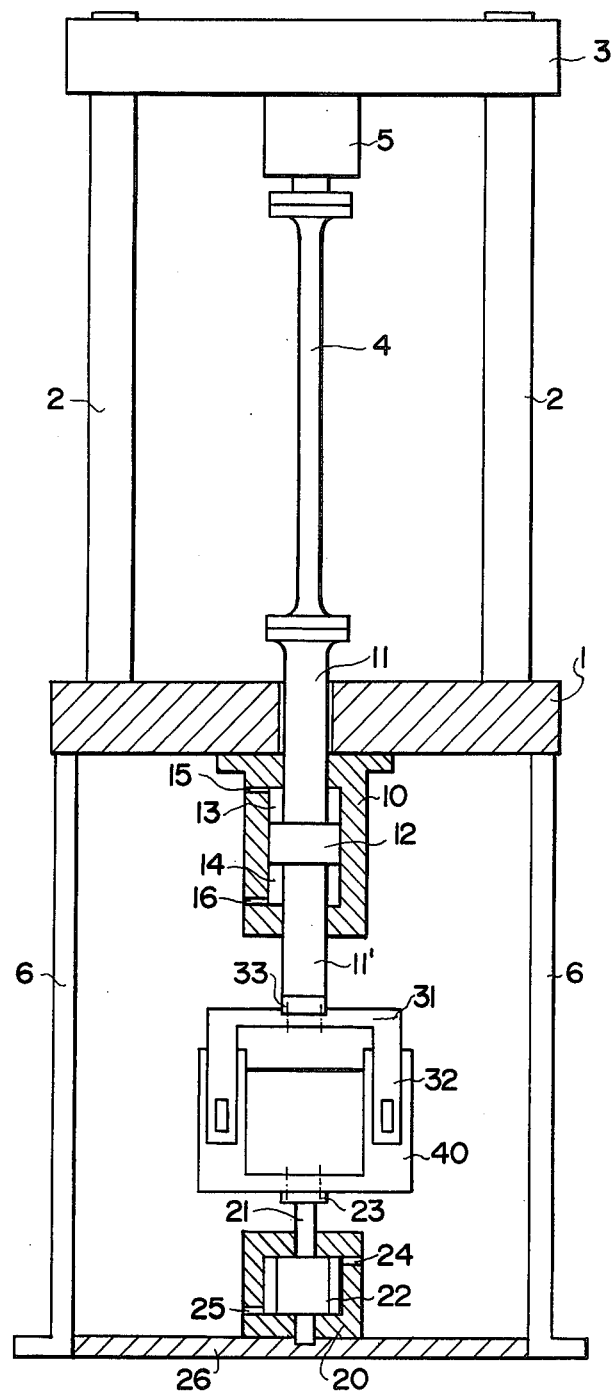
FIG. 5 shows substantially the view of FIG. 1, wherein the torque producing member is supported in the main machine frame and the secondary frame member is eliminated.

FIG. 5 shows an alternate embodiment wherein the torque producing cylinder 20 is connected to a base member 26 which may be part of the machine frame or part of the foundation. The arrangement is so constructed that the desired torque or rotary movement may be transmitted to the test sample 4. In this embodiment the secondary frame component 30 may be eliminated since the torque producing cylinder 20 is supported by the base member 26 and by the other frame components, e.g., the sub-frame 6 in a position opposite the longitudinal loading cylinder or opposite the main machine frame 1, 2, 3.

In the light of the above disclosure it will be appreciated that by making the guide roller bearings 43 adjustable under the force of the springs 47, a cooperation between the guide surfaces 34 of the fork ends 32 with the respective roller bearing is assured substantially free of play. Preferably the tiltable adjustable roller bearings 43 are supported in said housing 45 which is tiltable about an axis 46 extending in parallel to the rotational axis 43' of the respective roller bearing 43. Since the adjustable spring 47 is effective on the housing 45 a uniform force distribution is assured and jamming is avoided while simultaneously achieving a simple structure in which the friction forces are small when torque is transmitted.

Although the invention has been described with reference to specific example embodiments, it is to be understood that it is intended to cover all modifications and equivalents within the scope of the appended claims.

What is claimed is:

1. An apparatus for testing a sample by simultaneously loading said sample with longitudinal forces and with torque, comprising frame means, load means operatively secured to said frame means and connected for applying longitudinal forces to said sample, torque means operatively arranged in axial alignment with said load means for applying torque to the sample, said load means comprising first housing means and piston means including a first piston rod and a second piston rod extending out of said first housing means in opposite directions, said first piston rod being connected to the test sample, said apparatus further comprising fork means connected to said second piston rod and including fork ends for applying torque to said sample, said torque means comprising second housing means, rotary piston means operatively arranged in said second housing means, and means for transmitting torque to said fork means, said torque transmitting means being operatively connected to said rotary piston means and cooperating with said fork means for allowing longitudinal movement of said fork means relative to said torque means while simultaneously preventing rotation of said fork ends relative to said torque transmitting means.

2. The apparatus of claim 1, further comprising secondary frame means interconnecting said first housing means of said load means and said second housing means of said torque means, said secondary frame means comprising axially aligned holes, said second piston rod of said load means extending rotatably through one of said axially aligned holes, said torque transmitting means extending rotatably through the other of said holes.

3. The apparatus of claim 1 or 2, wherein said fork ends comprise outwardly facing bearing surfaces on opposite sides of each fork end, said torque transmitting means comprising respective bearing means for each fork end arranged for cooperation with said outwardly facing bearing surfaces, whereby said fork ends are guided along their bearing surfaces by said respective bearing means for relative longitudinal movement and whereby torque may be transmitted from said torque means to said sample.

4. The apparatus of claim 3, wherein said bearing means comprise two roller bearings for each fork end, means rigidly mounting one of said two roller bearings for cooperation with the respective bearing surface of the fork end, and further means mounting the other of said two roller bearings so that said other roller bearing is tiltable in the direction of the corresponding bearing surface.

5. The apparatus of claim 4, further comprising spring means operatively arranged for biasing said other roller bearing against the corresponding bearing surface.

6. The apparatus of claim 5, further comprising means arranged for adjusting said spring means for varying said biasing.

7. The apparatus of claim 5, wherein said further mounting means for said other roller bearing include bearing housing means and tilting axis means for said housing means, whereby said housing means is tiltable in the direction of the corresponding bearing surface about said tilting axis means which is arranged outside of but parallel to the axis of rotation of the respective roller bearing.

8. The apparatus of claim 7, wherein said spring means bias said bearing housing means against the corresponding bearing surface.

9. The apparatus of claim 1 or 2, wherein said torque transmitting means comprise hydrostatic bearing means operatively arranged for guiding the corresponding fork ends.

10. The apparatus of claim 9, further comprising housing means for said hydrostatic bearing means, and means arranged for adjusting the position of said hydrostatic bearing means in said housing means relative to said fork ends.

11. The apparatus of claim 1, wherein said frame means comprise support means, said torque means being arranged on said support means in such a position that said axial alignment of the torque means with the load means is assured.

12. The apparatus of claim 11, wherein said support means comprise a cross member at the base of said frame means, said torque means being centrally supported on said cross member.

* * * * *